(12) United States Patent
Lou et al.

(10) Patent No.: US 10,296,604 B2
(45) Date of Patent: May 21, 2019

(54) METHOD AND DEVICE FOR PROVIDING REFERENCE INFORMATION FOR SCAN PROTOCOL

(71) Applicant: Shenyang Neusoft Medical Systems Co., Ltd., Shenyang (CN)

(72) Inventors: Shanshan Lou, Shenyang (CN); Han Zheng, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 693 days.

(21) Appl. No.: 14/819,368

(22) Filed: Aug. 5, 2015

(65) Prior Publication Data

US 2016/0042012 A1 Feb. 11, 2016

(30) Foreign Application Priority Data

Aug. 6, 2014 (CN) .......................... 2014 1 0385398

(51) Int. Cl.
*G06F 17/30* (2006.01)
*G06F 19/00* (2018.01)
(Continued)

(52) U.S. Cl.
CPC ........ *G06F 17/30277* (2013.01); *A61B 6/032* (2013.01); *A61B 6/488* (2013.01);
(Continued)

(58) Field of Classification Search
CPC ............. G06F 17/30277; G06T 11/005; G06T 2200/04; G06T 2207/10081; G06T 2207/30204
(Continued)

(56) References Cited

U.S. PATENT DOCUMENTS 7,378,660 B2 * 5/2008 Case ................... G01T 1/1611
250/363.01
2006/0153436 A1 7/2006 Haras
(Continued)

FOREIGN PATENT DOCUMENTS

CN 100581472 C 1/2010
JP 2006192270 A 7/2006
(Continued)

OTHER PUBLICATIONS

The First Office Action dated Dec. 28, 2015 regarding the Chinese priority patent application (Appl. No. 201410385398.5).

*Primary Examiner* — Monica M Pyo
(74) *Attorney, Agent, or Firm* — Kilpatrick Townsend & Stockton LLP (57) ABSTRACT

A method and a device for providing reference information for a scan protocol are provided. The method includes: obtaining first basic information and a first pilot image of a patient to be scanned as index information; retrieving a second pilot image that matches the index information from a preset scan protocol database; and outputting a second pilot image, and a second reconstructed image and a second scan protocol in the preset scan protocol database which correspond to the second pilot image as reference information. If the second pilot image matches the index information, the physical condition of a scanned patient corresponding to the second pilot image is similar to that of the patient to be scanned, and the second pilot image, and the second reconstructed image and the second scan protocol in the preset scan protocol database which correspond to the second pilot image are outputted as reference information.

10 Claims, 4 Drawing Sheets

(51) Int. Cl.
*A61B 6/00* (2006.01)
*A61B 6/03* (2006.01)

(52) U.S. Cl.
CPC ............ *A61B 6/5211* (2013.01); *A61B 6/544* (2013.01); *G06F 19/321* (2013.01); *A61B 6/545* (2013.01)

(58) Field of Classification Search
USPC .......................................... 707/722; 382/131
See application file for complete search history.

(56) References Cited

U.S. PATENT DOCUMENTS

| | | | |
|---|---|---|---|
| 2006/0193437 A1* | 8/2006 | Boeing | A61B 6/032 378/115 |
| 2009/0074143 A1 | 3/2009 | Tsukagoshi et al. | |
| 2011/0150312 A1* | 6/2011 | Takanami | G06T 17/20 382/131 |
| 2011/0222749 A1* | 9/2011 | Franaszek | G06K 9/34 382/128 |
| 2013/0051704 A1 | 2/2013 | Koishi | |
| 2013/0101079 A1 | 4/2013 | Hough et al. | |
| 2015/0103969 A1* | 4/2015 | Flohr | A61B 6/032 378/4 |

FOREIGN PATENT DOCUMENTS

| | | |
|---|---|---|
| JP | 2013048746 A | 3/2013 |
| JP | 2015130909 A | 7/2015 |

* cited by examiner

METHOD AND DEVICE FOR PROVIDING REFERENCE INFORMATION FOR SCAN PROTOCOL

CROSS REFERENCE OF RELATED APPLICATION

The present application claims the priority to Chinese Patent Application No. 201410385398.5, titled "METHOD AND DEVICE FOR PROVIDING REFERENCE INFORMATION FOR SCAN PROTOCOL", filed on Aug. 6, 2014 with the State Intellectual Property Office of the PRC, which is incorporated herein by reference in its entirety.

BACKGROUND

To perform CT scan examination, a doctor generally sets a scan protocol based on basic information of a patient, such as the gender, a body part to be scanned and a scanning mode. A scan protocol includes a scanning voltage, a scanning current, a scanning duration and a scanning irradiation dose, and the like.

It is especially important to set the irradiation dose parameter in the scan protocol. If a low irradiation dose is applied to both a fat patient and a thin patient, a scan image noise of the fat patient is lager than that of the thin patient; and if a high irradiation dose is applied to both the fat patient and the thin patient, the irradiation dose is wasted for the thin patient and the thin patient is subjected to excessive and unnecessary radiation. Hence, a high irradiation dose should be applied to the fat patient, and a low irradiation dose should be applied to the thin patient.

However, different doctors may have significant subjective difference in determining a scan protocol for a patient due to their different working experiences. The differences between scan protocols set by different doctors for the patient, especially between the irradiation doses in the scan protocols, are significant. In this case, the set irradiation dose may be deficient such that definition of a CT image is negatively affected, or the set irradiation dose may be excessive such that the patient is subjected to redundant radiation.

DETAILED DESCRIPTION OF THE EMBODIMENTS

The present disclosure may make a doctor more accurately set a scan protocol for the patient to be scanned by providing the doctor with a second pilot image, a reconstructed image and a scan protocol of a scanned patient as reference information, where the scanned patient has similar physical condition to the patient to be scanned.

Examples of the present disclosure are explained in detail hereinafter in conjunction with the drawings.

Figure 1:
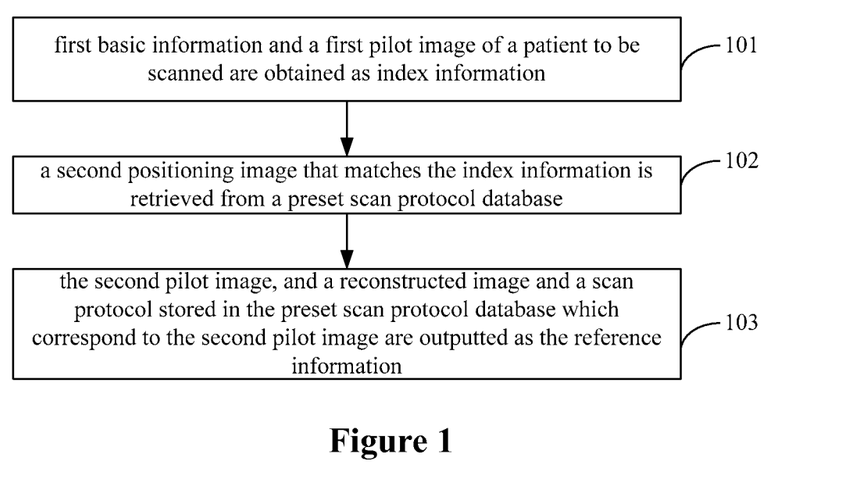
FIG. 1 is a flow chart of a method for providing reference information for a scan protocol according to an example of the present disclosure.

FIG. 1 is a flow chart of a method for providing reference information for a scan protocol according to a first example of the present disclosure. The method includes blocks 101-103.

block 101, a first basic information and a first pilot image of a patient to be scanned are obtained as index information.

A doctor should input the first basic information based on the physical condition of the patient to be scanned before CT scanning. The first basic information may affect the setting of the scan protocol. In an example, the first basic information may include the gender of the patient to be scanned, a to-be-scanned body part of the patient, and a scanning mode for the patient to be scanned.

Since men and women may have different somatotypes, contents of fat in muscle and anatomical structures, different scan protocols should be adopted even for the same body part to be scanned and the same scanning mode when considering different body structures of men and women. In addition, different scan protocols may be adopted for different body parts to be scanned and different scanning modes. The scanning mode may include a tomography scan and a spiral scan.

It should be understood that the first basic information may further include any one or any combination of parameters such as age, height, weight and Body Mass Index (BMI) of the patient to be scanned. The present disclosure is not limited specifically here.

The first pilot image of the patient to be scanned refers to the pilot image which is obtained by performing one scan such that a doctor may determine a body part of the patient to be scanned. The pilot image is different from a reconstructed image obtained finally after a CT scan. The pilot image is mainly used to determine a start point and a termination point of the CT scan so as to determine a scan scope. The first basic information and the first pilot image of the patient to be scanned are parameters greatly influencing the scan protocol. The first basic information and the first pilot image are used as index information to search for scan information of a scanned patient having similar physical condition to the patient to be scanned in a preset scan protocol database, and wherein the scan information of the scanned patient is taken as reference information.

block 102, a second pilot image that matches the index information is retrieved from a preset scan protocol database.

To provide reference information better, scan information of a large number of scanned patients is stored in the preset scan protocol database. In an example, the scan information includes second basic information, the second pilot image, a second reconstructed image and a second scan protocol of the scanned patient. Additionally, a correspondence among the second basic information, the second pilot image, the second reconstructed image and the second scan protocol of each scanned patient is also stored in the preset scan protocol database.

The scan protocol database may be preset based on acquired scan information of a large number of scanned patients. Alternatively, the scan protocol database may be gradually accumulated by storing the first basic information and the first pilot image of each patient to be scanned, a first scan protocol set based on the reference information and a first reconstructed image obtained by scanning each patient to be scanned according to the first scan protocol into the scan protocol database.

After the first scan protocol is set for the patient to be scanned based on the reference information, the first reconstructed image is obtained after scanning the patient to be scanned according to the first scan protocol; and after the first basic information, the first pilot image, the first scan protocol and the first reconstructed image are stored in the preset scan protocol database, the first basic information is taken as second basic information, the first pilot image is taken as a second pilot image, the first scan protocol is taken as a second scan protocol, and the first reconstructed image is taken as a second reconstructed image.

It is to be understood here that "first" and "second" herein are only used to distinguish scan information of the patient to be scanned from scan information of the scanned patient, and is not used to indicate an order.

In an example, the retrieving a second pilot image that matches the index information from a preset scan protocol database may include:

searching for second basic information matched with the first basic information in the preset scan protocol database;

obtaining a second pilot image corresponding to the second basic information which is matched with the first basic information; and determining whether the second pilot image matches the first pilot image, and determining the second pilot image as a second pilot image which matches the index information when the second pilot image matches the first pilot image.

After retrieving a second pilot image of a scanned patient matching the first pilot image of the patient to be scanned, the physical condition of the scanned patient is similar to that of the patient to be scanned.

block 103: the second pilot image, and a reconstructed image and a scan protocol stored in the preset scan protocol database which correspond to the second pilot image are outputted as the reference information.

If the second basic information of the scanned patient and the second pilot image of the scanned patient respectively match the first basic information and the first pilot image of the patient to be scanned, it means that the physical condition of the scanned patient in the preset scan protocol database is similar to that of the patient to be scanned. The second pilot image, the second reconstructed image and the second scan protocol of the scanned patient in the preset scan protocol database who has the similar physical condition to the patient to be scanned are outputted as the reference information. Since the correspondence among the second basic information, the second pilot image, the second reconstructed image and the second scan protocol of each scanned patient is stored in the preset scan protocol database, if a second pilot image which matches the first pilot image of the patient to be scanned is retrieved, the second reconstructed image and the second scan protocol corresponding to the second pilot image may be obtained.

In another example, the outputted reference may also include a dose report besides the second pilot image, and the second reconstructed image and the second scan protocol in the preset scan protocol database which correspond to the second pilot image. The doctor may obtain an irradiation dose value of the scanned patient from the dose report directly, rather than convert an irradiation dose parameter in the second scan protocol to the irradiation dose value. As a reference for the irradiation dose value, the dose report is more intuitive than the irradiation dose parameter in the second scan protocol.

When multiple second pilot images matching the index information may be retrieved from a preset scan protocol database, it means there are multiple scanned patients whose physical conditions are similar to that of the patient to be scanned. Multiple pieces of reference information may be outputted in a descending order of matching degrees between the first pilot image of the patient to be scanned and the multiple second pilot images; or multiple pieces of reference information may be outputted in an ascending order or in a descending order of irradiation dose parameters in multiple second scan protocols; or an outputting order of multiple pieces of reference information may be set in other manners according to actual needs. Alternatively, one or more scanned patients may be selected, according to a self-set condition, from the multiple scanned patients whose physical conditions are similar to that of the patient to be scanned, and reference information of the selected one or more scanned patients is output, which is not limited specifically here.

The second pilot image, the second constructed image and the second scan protocol of one or more scanned patients who have similar physical condition to the patient to be scanned are outputted for the doctor as the reference information. Based on the reference information of the one or more scanned patients, the doctor may set the first scan protocol of the patient to be scanned, especially set an irradiation dose parameter in the first scan protocol according actual needs. On the premise that the irradiation dose parameter set by the doctor based on the reference information can ensure a clear reconstructed image for one body part to be scanned, the irradiation dose parameter is set appropriately such that the irradiation dose is neither deficient nor excessive, improving accuracy of the scan protocol which is set by the doctor for the patient to be scanned.

For a same patient to be scanned, a matching second pilot image which is retrieved from the preset scan protocol database may not change, that is, same reference information is outputted for different doctors; accordingly, different doctors may set the first scan protocol for the patient to be scanned based on the same reference information. Therefore, subjective effects of different doctors on setting the scan protocol, especially the irradiation dose parameter in the scan protocol, for the same patient to be scanned can be eliminated to some extent.

As can be seen from above description, the present disclosure has following advantageous effect.

The first basic information and the first pilot image of the patient to be scanned are obtained as index information; the second pilot image that matches the index information is retrieved from the preset scan protocol database; and the second pilot image, and the second reconstructed image and the second scan protocol in the preset scan protocol database which correspond to the second pilot image are outputted as reference information. If the second pilot image matches the index information, the physical condition of the scanned patient corresponding to the second pilot image is similar to that of the patient to be scanned, and the second pilot image, and the second reconstructed image and the second scan protocol in the preset scan protocol database which correspond to the second pilot image are outputted as the reference information, for helping the doctor in determining the scan protocol of the patient to be scanned, preventing the irradiation dose from being deficient or excessive, and improving accuracy of the scan protocol which is set by the doctor for the patient to be scanned.

Figure 2:
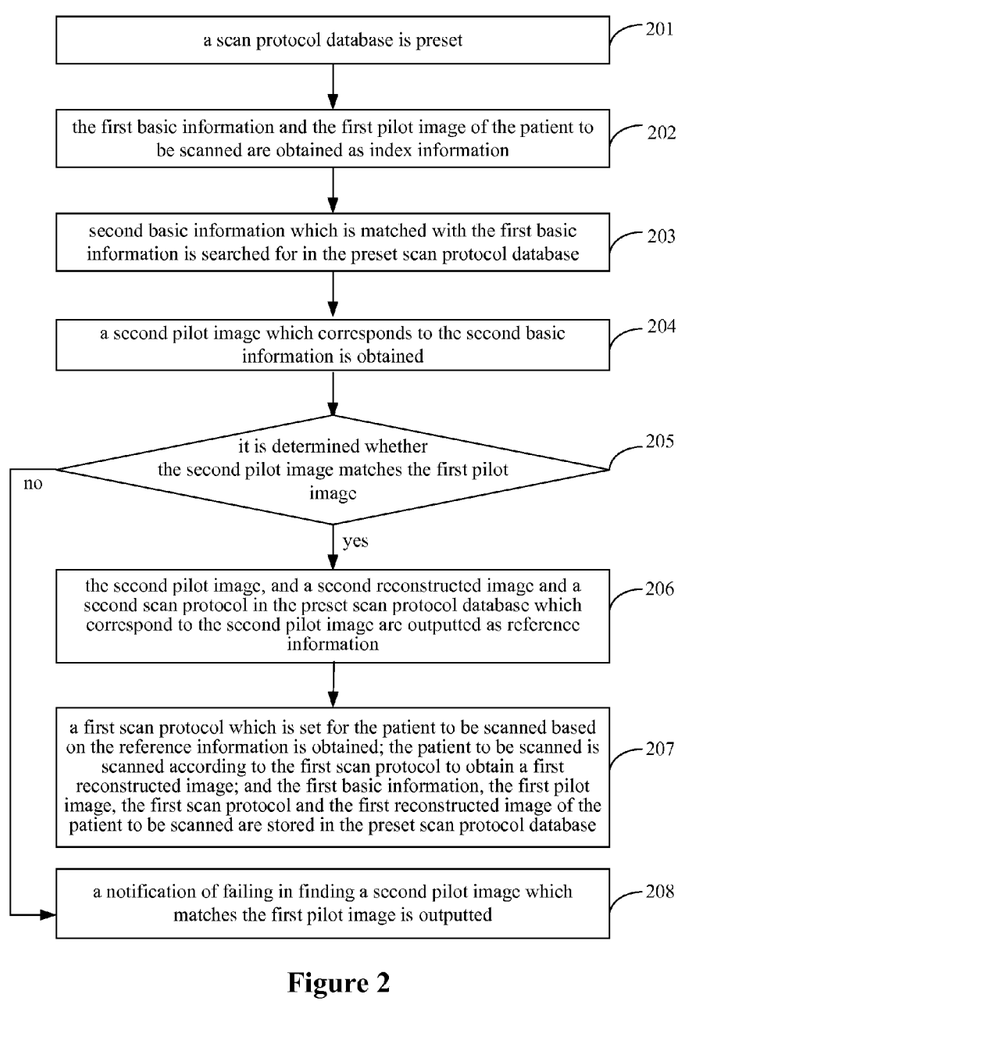
FIG. 2 is a flow chart of a method for providing reference information for a scan protocol according to another example of the present disclosure.

FIG. 2 is a flow chart of a method for providing reference information for a scan protocol according to a second example of the present disclosure. Compared with the first example described above, in this example, a specific implementation of retrieving a second pilot image that matches the index information from a preset scan protocol database is provided. The method according to the second example includes following blocks 201 to 208.

block 201, a scan protocol database is preset, where a correspondence among second basic information, a second pilot image, a second reconstructed image and a second scan protocol of each scanned patient is stored in the preset scan protocol database.

Scan information of multiple scanned patients is stored in the preset scan protocol database. Scan information of each scanned patient includes the second basic information, the second pilot image, the second reconstructed image and the second scan protocol. The correspondence among the second basic information, the second pilot image, the second reconstructed image and the second scan protocol of each scanned patient is stored in the preset scan protocol database.

In general, the preset scan protocol database is preset by obtaining scan information of a large number of scanned patients. Since the scan information of a large number of scanned patients is stored in the preset scan protocol database, it is easier to retrieve a second pilot image of a scanned patient matching a first pilot image of a patient to be scanned, on the premise that the second basic information of the scanned patient is matched with first basic information of the patient to be scanned. In other words, it is easier to find a scanned patient whose physical condition is similar to that of the patient to be scanned and the scan information of the found scanned patient is taken as the reference information.

block 202, the first basic information and the first pilot image of the patient to be scanned are obtained as index information.

The first basic information includes the gender of the patient to be scanned, a to-be-scanned body part of the patient, and a scanning mode for the patient to be scanned. The first basic information has greater influence on the setting of the scan protocol, and thus has relative high referential value. Further, the first basic information may also include any one or any combination of parameters such as age, height, weight and BMI of the patient to be scanned. The first pilot image is mainly used to determine a scan scope of the patient to be scanned.

block 203, second basic information which is matched with the first basic information is searched for in the preset scan protocol database.

A first step of retrieving the scanned patient whose physical condition is similar to that of the patient to be scanned in the scan image database is to search for second basic information which is matched with the first basic information of the patient to be scanned. The first basic information and the second basic information may include the gender, a body part to be scanned and a scanning mode.

The searching for the second basic information which is matched with the first basic information in the preset scan protocol database may include:

determining whether the gender in the first basic information is the same as the gender in the second basic information;

determining whether the body part to be scanned in the first basic information is the same as the body part to be scanned in the second basic information;

determining whether the scanning mode in the first basic information is the same as the scanning mode in the second basic information; and determining that the second basic information is matched with the first basic information, if the gender, the body part to be scanned and the scanning mode in the first basic information are the same as those in the second basic information respectively.

The execution order to determine whether the gender, the body part to be scanned and the scanning mode in the first basic information are the same as those in the second basic information respectively is not limited specifically, and it may be set according to actual need. In generally, the execution order may be performed as follows.

block 1, it is determined whether the gender in the first basic information is the same as the gender in the second basic information. If the gender in the first basic information is the same as the gender in the second basic information, block 2 is performed; or it is determined that the first basic information is not matched with the second basic information if the gender in the first basic information is not the same as the gender in the second basic information.

block 2, it is determined whether the body part to be scanned in the first basic information is the same as the body part to be scanned in the second basic information. If the body part to be scanned in the first basic information is the same as the body part to be scanned in the second basic information, block 3 is performed; or it is determined that the first basic information is not matched with the second basic information if the body part to be scanned in the first basic information is not the same as the body part to be scanned in the second basic information.

block 3, it is determined whether the scanning mode in the first basic information is the same as the scanning mode in the second basic information; If the scanning mode in the first basic information is the same as the scanning mode in the second basic information, it is determined that the first basic information is matched with the second basic information; or it is determined that the first basic information is not matched with the second basic information if the scanning mode in the first basic information is not the same as the scanning mode in the second basic information.

It should be understood that if the basic information includes parameters such as age, height, weight and BMI, etc., the searching for second basic information which is matched with the first basic information in the preset scan protocol database may further include:

determining whether the age in the first basic information is the same as the age in the second basic information;

determining whether the height in the first basic information is the same as the height in the second basic information;

determining whether the weight in the first basic information is the same as the weight in the second basic information; and determining whether the BMI in the first basic information is the same as the BMI in the second basic information.

It should be understood that the execution order of above determination procedures is not limited specifically, and it may be set according to actual need. It is determined that the first basic information is matched with the second basic information, if the gender, the body part to be scanned and the scanning mode in the first basic information are respectively same as those in the second basic information, and the age, the height, the weight and BMI in the first basic information of the patient to be scanned are also same as those in the second basic information of the scanned patient respectively.

block 204, a second pilot image which corresponds to the second basic information is obtained.

A second step of retrieving the scanned patient whose physical condition is similar to that of the patient to be scanned in the scan image database is to obtain the second pilot image that corresponds to the second basic information which is matched with the first basic information of the patient to be scanned. It should be understood that there may be multiple pieces of second basic information in the preset scan protocol database which are matched with the first basic information of the patient to be scanned. In other words, generally, there may be multiple scanned patients whose second basic information is matched with the first basic information. Second pilot images which correspond to the second basic information of the multiple scanned patients may be obtained respectively, i.e., the second pilot images of the multiple scanned patients may be obtained.

block 205, it is determined whether the second pilot image matches the first pilot image. If the second pilot image matches the first pilot image, block 206 is performed; or else block 208 is performed.

A third step of retrieving the scanned patient whose physical condition is similar to that of the patient to be scanned in the scan image database is to determine whether the second pilot image of each scanned patient matches the first pilot image one by one. If a second pilot image matches the first pilot image, it may be considered that physical condition of a scanned patient who has the second pilot image is similar to that of the patient to be scanned.

Specifically, the determining whether the second pilot image matches the first pilot image may include block A and block B.

block A, an image deviation between a location parameter of a preset characteristic location in the second pilot image and a location parameter of a preset characteristic location in the first pilot image is calculated.

block B, it is determined whether the image deviation is less than a preset threshold, and it is determined that the second pilot image matches the first pilot image if the image deviation is less than a preset threshold.

The preset characteristic location greatly affects the quality of the reconstructed image as the irradiation dose varies. The preset characteristic location is usually preset in the pilot image according to experience. In general, there is little difference between the preset characteristic location in the first pilot image of the patient to be scanned and the preset characteristic location in the second pilot image of the scanned patient.

Figure 3:
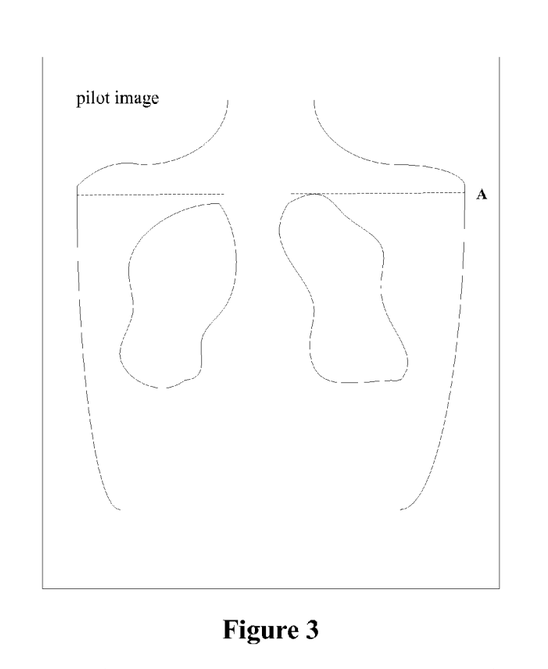
FIG. 3 is a scan image of chest, which is taken as a pilot image according to the present disclosure.

An approach for selecting the preset characteristic location in the pilot image is illustrated hereinafter in conjunction with the drawings. For example, FIG. 3 is a scan image of chest which is used as a pilot image. Lung tissue is segmented out from the pilot image by performing image segmentation on the pilot image, and the top of the lung lobe is selected as the preset characteristic location. In general, the preset characteristic location is selected based on the principle of human anatomy. In this example, it assumes that the selected preset characteristic location is located near the collarbones and shoulders. The density and size of the preset characteristic location are larger than those of other locations; if a low irradiation dose is adopted in a chest CT scan, strip artifacts may be caused due to lack of irradiation, which has great influence on the quality of the reconstructed image of the CT scan.

Figure 4:
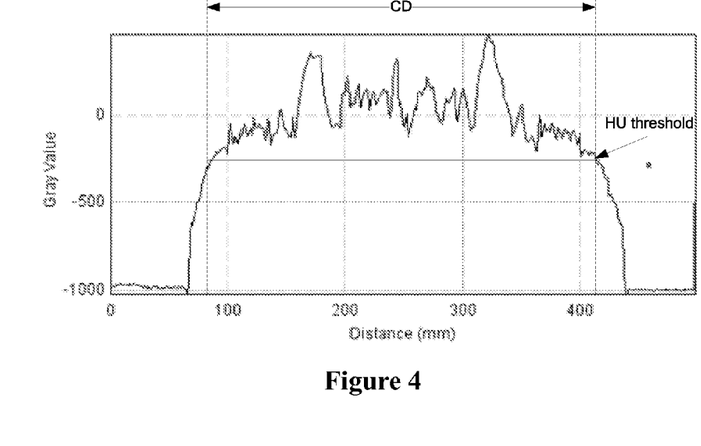
FIG. 4 is a graph of CT scan values corresponding to the pilot image in FIG. 3 of the present disclosure.

In general, the location parameter of the preset characteristic location may include a size and an attenuation mean value. The size refers to the length between a head index point and a tail index point within the preset characteristic location, where CT scan values are greater than a threshold value. Reference can be made to FIG. 4, which is a graph of CT scan values corresponding to the pilot image of FIG. 3. In FIG. 3, a straight line A is the preset characteristic location and a threshold T is preset. Points of the graph in FIG. 4 are traversed from a start point to a central point to find the head index point at which the CT scan value firstly exceeds the threshold T, and points of the graph in FIG. 4 are traversed from an end point to the central point to find the tail index point at which the CT scan value firstly exceeds the threshold T. As is shown in FIG. 4, the head index point is C, and the tail index point is D, so the length between C and D is the size in the location parameter of the preset characteristic location. The sum of the mean of the CT scan values at points between C and D in FIG. 4 and 1024 HU is the attenuation mean value.

The above approach may be used to calculate a first size and a first attenuation mean value in the location parameter of the preset characteristic location in the first pilot image of the patient to be scanned, and also may be used to calculate a second size and a second attenuation mean value in the location parameter of the preset characteristic location in the second pilot image of each of multiple scanned patients.

Accordingly, block A may include:

calculating a first size and a first attenuation mean value of the preset characteristic location in the first pilot image;

calculating a second size and a second attenuation mean value of the preset characteristic location in the second pilot image;

calculating a ratio of an absolute value of a difference between the first size and the second size to the first size as a first sub-deviation;

calculating a ratio of an absolute value of a difference between the first attenuation mean value and the second attenuation mean value to the first attenuation mean value as a second sub-deviation; and calculating the sum of the first sub-deviation and the second sub-deviation as the image deviation.

The first size and the first attenuation mean value of the preset characteristic location in the first pilot image of the patient to be scanned are calculated with the above approach, where the first size is represented by $L_0$, and the first attenuation mean value is represented by $A_0$. The second size and the second attenuation mean value of the preset characteristic location in the first pilot image of each patient to be scanned is calculated with the above approach, where the second size is represented by $L$, and the second attenuation mean value is represented by $A$.

The ratio of an absolute value of the difference between the first size and the second size to the first size is calculated, using formula (1), as the first sub-deviation, where formula (1) is given as follows:

$$\left| \frac{L - L_0}{L_0} \right|. \tag{1}$$

The ratio of an absolute value of the difference between the first attenuation mean value and the second attenuation mean value to the first attenuation mean value is calculated, using formula (2), as the second sub-deviation, where formula (2) is given as follows:

$$\left| \frac{A - A_0}{A_0} \right|. \tag{2}$$

The image deviation E between the first pilot image of the patient to be scanned and the second pilot image of each scanned patient may be calculated using formula (3):

$$E = \left|\frac{L-L_0}{L_0}\right| + \left|\frac{A-A_0}{A_0}\right|. \quad (3)$$

As can be seen, the image deviation E is the sum of sub-deviation between respective items of the location parameter of the first pilot image and respective items of the location parameter of the second pilot image. In general, the location parameter may include the size and the attenuation mean value, and may also include other item. If the location parameter includes other item, a sub-deviation of the other item may be calculated and added.

If the image deviation between the location parameter of the preset characteristic location in the second pilot image and the location parameter of the preset characteristic location in the first pilot image is obtained, block B is performed to determine whether the image deviation is less than the preset threshold. It means that the second pilot image matches the first pilot image and the physical condition of the patient to be scanned is similar to that of the scanned patient, if the image deviation is less than the preset threshold. It means that the second pilot image does not match the first pilot image and there is a relative great difference between the physical condition of the patient to be scanned and the physical condition of the scanned patient if the image deviation is not less than the preset threshold.

block 206, the second pilot image, and a second reconstructed image and a second scan protocol in the preset scan protocol database which correspond to the second pilot image are outputted as reference information.

The second pilot image of each scanned patient that matched with the first pilot image of a patient to be scanned, and the second reconstructed image and the second scan protocol in the preset scan protocol database which correspond to the second pilot image may be outputted as the reference information. Alternatively, one or more of the second pilot image of the selected one or more scanned patients according to actual needs, and the second reconstructed image and the second scan protocol in the preset scan protocol database which correspond to the second pilot image may be outputted as reference information.

In another example, a selection condition may be preset by a doctor, and a scan protocol of a scanned patient is automatically selected as a scan protocol of the patient to be scanned. First, the preset selection condition is obtained, and then the scan protocol of a patient to be scanned is determined from the reference information according to the preset selection condition.

In this example, the selection condition may be the irradiation dose parameter of the scan protocol. For example, a scan protocol having a maximum dose parameter or a minimum dose parameter is selected as the scan protocol of the patient to be scanned. It is understood that the selection condition may be set in other ways, which are not detailed here.

block 207, a first scan protocol which is set for the patient to be scanned based on the reference information is obtained; the patient to be scanned is scanned according to the first scan protocol to obtain a first reconstructed image; and then the first basic information, the first pilot image, the first scan protocol and the first reconstructed image of the patient to be scanned are stored in the preset scan protocol database.

After the first scan protocol has been set for the patient to be scanned, a CT scan may be performed on the patient to be scanned according to the first scan protocol to obtain the first reconstructed image of the patient to be scanned, and then the first basic information, the first pilot image, the first scan protocol and the first reconstructed image of the patient to be scanned are stored in the preset scan protocol database in order to enrich the data continually. Once the CT scan is accomplished and the above items are stored in the preset scan protocol database, the first basic information is taken as second basic information, the first pilot image is taken as a second pilot image, the first scan protocol is taken as a second scan protocol, and the first reconstructed image is taken as a second reconstructed image.

block 208, a notification of failing in finding a second pilot image which matches the first pilot image is outputted.

In the case that no second pilot image matching the first pilot image is found, the notification of failing in finding a second pilot image which matches the first pilot image is outputted, and the doctor may manually set a scan protocol based on the specific condition of the patient to be scanned.

As can be seen, the present disclosure also has the following advantageous effect.

With the method according to this example, the scan information such as the second pilot image, the reconstructed image and the second scan protocol of the scanned patient who has the similar physical condition to the patient to be scanned may be retrieved and outputted as reference information for setting a scan protocol for the patient to be scanned. In addition, the first basic information, the first pilot image, the first scan protocol and the first reconstructed image of the patient to be scanned are stored in the preset scan protocol database, thereby enriching the data in the preset scan protocol database continually.

Figure 5:
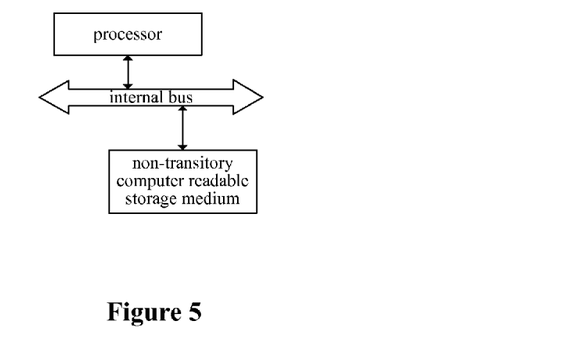
FIG. 5 is a schematic structural diagram of a device for providing reference information for a scan protocol according to an example of the present disclosure.

FIG. 5 is a schematic structural diagram of a device for providing reference information for a scan protocol according to a third example of the present disclosure. The device corresponds to the method according to the first example. The device includes a processor and a non-transitory computer readable storage medium, where instructions are stored in the non-transitory computer readable storage medium. The processor may communicate with the non-transitory computer readable storage medium through an internal bus.

The processor may read the instructions to obtain first basic information and a first pilot image of a patient to be scanned as index information;

retrieve a second pilot image that matches the index information from a preset scan protocol database.

The processor reads the instructions to retrieve a second pilot image that matches the index information from a preset scan protocol database is to:

search, in the preset scan protocol database, for second basic information which is the matched with the first basic information;

obtain a second pilot image corresponding to the second basic information; and determine whether the second pilot image matches the first pilot image, and determine the second pilot image as a second pilot image which matches the index information if the second pilot image matches the first pilot image.

The processor may read the instructions further to output the second pilot image, and a second reconstructed image and a second scan protocol in the preset scan protocol database which correspond to the second pilot image as reference information.

The third example is similar to the first example. Details of the third example are not given here and can be known with reference to the description of the first example.

A device for providing reference information for a scan protocol is provided according to a fourth example of the present disclosure. The device corresponds to the method according to the second example. Similar to the third example, the device according to the fourth example also includes a processor and a non-transitory computer readable storage medium, where instructions are stored in the non-transitory computer readable storage medium, and the processor may communicate with the non-transitory computer readable storage medium through an internal bus.

The processor may read the instructions to preset a scan protocol database, where a correspondence among second basic information, a second pilot image, a second reconstructed image and a second scan protocol of each scanned patient is stored in the preset scan protocol database.

Figure 6:
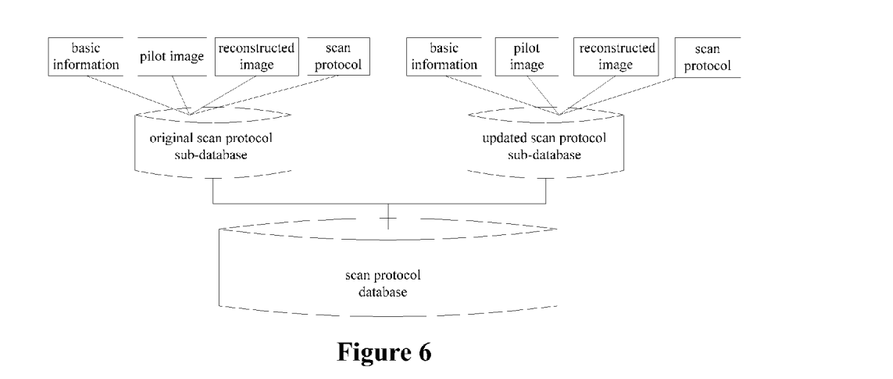
FIG. 6 is a schematic structural diagram of a scan protocol database provided in the present disclosure.

As shown in FIG. 6, the preset scan protocol database includes two parts. One part is an original scan protocol sub-database 601, in which scan data of a number of scanned patients is stored in advance. Scan data of each scanned patient includes the basic information, the pilot image, the scan protocol and the reconstructed image of the scanned patient. The other part is an updated scan protocol database 602. Scan data of each patient to be scanned is stored in the updated scan protocol database. The scan data of each patient to be scanned includes the basic information, the pilot image, the scan protocol and the reconstructed image of the patient to be scanned.

The processor may read the instructions further to: obtain first basic information and a first pilot image of a patient to be scanned as index information; and search, in the preset scan protocol database, for second basic information which is matched with the first basic information.

In an example, the processor reads the instructions to search, in the preset scan protocol database, for second basic information which is matched with the first basic information is to:

determine whether the gender in the first basic information is the same as the gender in the second basic information;

determine whether a body part to be scanned in the first basic information is the same as a body part to be scanned in the second basic information;

determine whether a scanning mode in the first basic information is the same as a scanning mode in the second basic information; and determine the second basic information which is matched with the first basic information if the gender, the body part to be scanned and the scanning mode in the first basic information are the same as those in the second basic information respectively.

The processor may read the instructions further to: obtain a second pilot image corresponding to the second basic information; and determine whether the second pilot image matches the first pilot image, and determine the second pilot image as a second pilot image which matches the index information if the second pilot image matches the first pilot image.

In an example, the processor reads the instructions to determine whether the second pilot image matches the first pilot image is to:

calculate an image deviation between a location parameter of a preset characteristic location in the second pilot image and a location parameter of a preset characteristic location in the first pilot image; and determine whether the image deviation is less than a preset threshold, and determine that the second pilot image matches the first pilot image if the image deviation is less than a preset threshold.

In an example, the processor reads the instructions to calculate an image deviation between a location parameter of a preset characteristic location in the second pilot image and a location parameter of a preset characteristic location in the first pilot image is to:

calculate a first size and a first attenuation mean value of the preset characteristic location in the first pilot image;

calculate a second size and a second attenuation mean value of the preset characteristic location in the second pilot image;

calculate a ratio of an absolute value of a difference between the first size and the second size to the first size as a first sub-deviation;

calculate a ratio of an absolute value of a difference between the first attenuation mean value and the second attenuation mean value to the first attenuation mean value as a second sub-deviation; and calculate a sum of the first sub-deviation and the second sub-deviation as the image deviation.

The processor may read the instructions further to output the second pilot image, and a second reconstructed image and a second scan protocol in the preset scan protocol database which correspond to the second pilot image as reference information.

In another example, the processor may read the instructions further to:

obtain a preset selection condition;

select a scan protocol of the patient to be scanned based on the reference information according to the preset selection condition;

obtain a first scan protocol which is set for the patient to be scanned based on the reference information;

scan the patient to be scanned according to the first scan protocol to obtain a first reconstructed image; and store the first basic information, the first pilot image, the first scan protocol and the first reconstructed image of the patient to be scanned in the preset scan protocol database.

The fourth example is similar to the second example. Details of the fourth example are not given here and can be known with reference to the description of the second example.

Those examples described above are only preferred embodiments of the present disclosure. It should be noted that improvements and modifications made by the skilled in the art without departing from the principle of the disclosure should fall within the scope of protection of the present disclosure. Moreover, the terminologies of "comprise", "include", and any other variants are intended be non-exclusive, so that the processes, methods, articles or equipment including a series of elements not only include those elements but also include other elements that are not clearly listed or elements which are inherent in the processes, methods, articles or equipment. In the case of no more restrictions, the elements defined by the statement "include a . . . " do not exclude that other similar elements may also exist in the processes, methods, articles or equipment including the listed elements.

The invention claimed is:

1. A method for providing reference information for a scan protocol, in a CT scanning machine, comprising:

presetting a scan protocol database, wherein a correspondence among second basic information, a second pilot image, a second reconstructed image and a second scan protocol of each scanned patient is stored in the preset scan protocol database;

obtaining first basic information and a first pilot image of the patient to be scanned as index information, wherein the pilot image is used to determine a start point and a termination point of CT scan so as to determine a scan scope;

retrieving the second pilot image that matches the index information from the preset scan protocol database;

outputting the second pilot image, and the second reconstructed image and the second scan protocol in the preset scan protocol database which correspond to the second pilot image as reference information;

obtaining, based on the reference information, a first scan protocol which is set for the patient to be scanned;

scanning the patient to be scanned according to the first scan protocol to obtain a first reconstructed image; and storing the first basic information, the first pilot image, the first scan protocol and the first reconstructed image of the patient to be scanned into the preset scan protocol database, wherein the retrieving a second pilot image that matches the index information in said preset scan protocol database comprises:

searching, in the preset scan protocol database, for second basic information which is matched with the first basic information;

obtaining a second pilot image corresponding to the second basic information; and determining whether the second pilot image matches the first pilot image, and determining the second pilot image as a second pilot image which matches the index information if the second pilot image matches the first pilot image.

2. The method according to claim 1, wherein the searching, in the preset scan protocol database, for second basic information which matched with the first basic information comprises:

determining whether a gender in the first basic information is the same as a gender in the second basic information;

determining whether a body part to be scanned in the first basic information is the same as a body part to be scanned in the second basic information;

determining whether a scanning mode in the first basic information is the same as a scanning mode in the second basic information; and determining that the second basic information is matched with the first basic information, if the gender, the body part to be scanned and the scanning mode in the first basic information are the same as the gender, body part to be scanned and the scanning mode in the second basic information respectively.

3. The method according to claim 1, wherein the determining whether the second pilot image matches the first pilot image comprises:

calculating an image deviation between a location parameter of a preset characteristic location in the second pilot image and a location parameter of a preset characteristic location in the first pilot image; and determining whether the image deviation is less than a preset threshold, and determining that the second pilot image matches the first pilot image if the image deviation is less than the preset threshold.

4. The method according to claim 3, wherein the calculating an image deviation between a position parameter of a preset characteristic position in the second pilot image and a position parameter of a preset characteristic position in the first pilot image comprises:

calculating a first size and a first attenuation mean value of the preset characteristic location in the first pilot image;

calculating a second size and a second attenuation mean value of the preset characteristic location in the second pilot image;

calculating a ratio of an absolute value of a difference between the first size and the second size to the first size as a first sub-deviation;

calculating a ratio of an absolute value of a difference between the first attenuation mean value and the second attenuation mean value to the first attenuation mean value as a second sub-deviation; and calculating a sum of the first sub-deviation and the second sub-deviation as the image deviation.

5. The method according to claim 1, further comprising:
obtaining a preset selection condition; and
determining the scan protocol of a patient to be scanned based on the reference information according to the preset selection condition.

6. A device for providing reference information for a scan protocol, in a CT scanning machine, comprising a processor and a non-transitory computer readable storage medium, wherein instructions are stored in the non-transitory computer readable storage medium and the processor reads the instructions to:

preset a scan protocol database, wherein a correspondence among second basic information, a second pilot image, a second reconstructed image and a second scan protocol of each scanned patient is stored in the preset scan protocol database;

obtain first basic information and a first pilot image of a patient to be scanned as index information, wherein the pilot image is used to determine a start point and a termination point of CT scan so as to determine a scan scope;

retrieve the second pilot image that matches the index information from the preset scan protocol database;

output the second pilot image, and the second reconstructed image and the second scan protocol in the preset scan protocol database which correspond to the second pilot image as reference information;

obtain, based on the reference information, a first scan protocol which is set for the patient to be scanned;

scan the patient to be scanned according to the first scan protocol to obtain a first reconstructed image; and store the first basic information, the first pilot image, the first scan protocol and the first reconstructed image of the patient to be scanned into the scan protocol database, wherein said processor reads the instructions to retrieve a second pilot image that matches the index information from a preset scan protocol database is to:

search, in the preset scan protocol database, for second basic information which is matched with the first basic information;

obtain a second pilot image corresponding to the second basic information; and determine whether the second pilot image matches the first pilot image, and determine the second pilot image as a second pilot image which matches the index information if the second pilot image matches the first pilot image.

7. The device according to claim 6, wherein said processor reads the instructions to search, in the preset scan protocol database, for second basic information which is matched with the first basic information is to:
- determine whether a gender in the first basic information is the same as a gender in the second basic information;
- determine whether a body part to be scanned in the first basic information is the same as a body part to be scanned in the second basic information;
- determine whether a scanning mode in the first basic information is the same as a scanning mode in the second basic information;
- determine the second basic information which is matched with the first basic information if the gender, the body part to be scanned and the scanning mode in the first basic information are the same as the gender, the body part to be scanned and the scanning mode in the second basic information respectively.

8. The device according to claim 6, wherein said processor reads the instructions to determine whether the second pilot image matches the first pilot image is to:
- calculate an image deviation between a location parameter of a preset characteristic location in the second pilot image and a location parameter of a preset characteristic location in the first pilot image; and
- determine whether the image deviation is less than a preset threshold, and determine that the second pilot image matches the first pilot image if the image deviation is less than the preset threshold.

9. The device according to claim 8, wherein said processor reads the instructions to calculate an image deviation between a location parameter of a preset characteristic location in the second pilot image and a location parameter of a preset characteristic location in the first pilot image is to:
- calculate a first size and a first attenuation mean value of the preset characteristic location in the first pilot image;
- calculate a second size and a second attenuation mean value of the preset characteristic location in the second pilot image;
- calculate a ratio of an absolute value of a difference between the first size and the second size to the first size as a first sub-deviation;
- calculate a ratio of an absolute value of a difference between the first attenuation mean value and the second attenuation mean value to the first attenuation mean value as a second sub-deviation; and
- a summation sub-unit, configured to calculating a sum of the first sub-deviation and the second sub-deviation as the image deviation.

10. The device according to claim 6, wherein said processor reads the instructions further to:
- obtain a preset selection condition; and
- select a scan protocol of the patient to be scanned based on the reference information according to the preset selection condition.

* * * * *